US008393229B2

(12) United States Patent
Tao et al.

(10) Patent No.: US 8,393,229 B2
(45) Date of Patent: Mar. 12, 2013

(54) SOFT PRESSURE SENSING DEVICE

(75) Inventors: Xiaoming Tao, Hong Kong (HK); Yangyong Wang, Hong Kong (HK); Tao Hua, Hong Kong (HK); Bo Zhu, Hong Kong (HK); Qiao Li, Hong Kong (HK)

(73) Assignee: The Hong Kong Research Institute of Textiles and Apparel Limited, Kowloon (HK)

( * ) Notice: Subject to any disclaimer, the term of this patent is extended or adjusted under 35 U.S.C. 154(b) by 433 days.

(21) Appl. No.: 12/712,123

(22) Filed: Feb. 24, 2010

(65) Prior Publication Data
US 2011/0203390 A1 Aug. 25, 2011

(51) Int. Cl.
G01L 1/00 (2006.01)
G01L 3/00 (2006.01)

(52) U.S. Cl. ............................. 73/862.046; 73/862.632

(58) Field of Classification Search ............ 73/862.041–862.046, 862.621, 862.627, 862.628, 862.632, 73/862.636, 862.637
See application file for complete search history.

(56) References Cited

U.S. PATENT DOCUMENTS

| | | | | |
|---|---|---|---|---|
| 3,448,424 A | * | 6/1969 | Laimins | 338/5 |
| 4,208,648 A | * | 6/1980 | Naumann | 338/99 |
| 4,492,949 A | * | 1/1985 | Peterson et al. | 338/114 |
| 4,509,527 A | * | 4/1985 | Fraden | 600/484 |
| RE32,180 E | * | 6/1986 | Lewiner et al. | 340/573.1 |
| 4,793,193 A | * | 12/1988 | Borgudd | 73/862.043 |
| 4,996,511 A | * | 2/1991 | Ohkawa et al. | 338/114 |
| 5,060,527 A | | 10/1991 | Burgess | |
| 5,431,571 A | * | 7/1995 | Hanrahan et al. | 439/91 |
| 5,512,716 A | * | 4/1996 | Buchien | 200/86 R |
| 5,695,859 A | * | 12/1997 | Burgess | 428/209 |
| 5,828,289 A | * | 10/1998 | Burgess | 338/47 |
| 5,886,615 A | * | 3/1999 | Burgess | 338/114 |
| 5,910,355 A | * | 6/1999 | Burgess | 428/209 |
| 5,962,118 A | * | 10/1999 | Burgess | 428/308.4 |
| 6,072,130 A | * | 6/2000 | Burgess | 200/86 R |
| 6,114,645 A | * | 9/2000 | Burgess | 200/512 |
| 6,360,612 B1 | * | 3/2002 | Trantzas et al. | 73/753 |
| 6,543,299 B2 | | 4/2003 | Taylor | |
| 6,807,869 B2 | * | 10/2004 | Farringdon et al. | 73/862.046 |
| 6,826,968 B2 | | 12/2004 | Manaresi et al. | |
| 7,153,383 B2 | * | 12/2006 | Gebert | 156/249 |
| 7,301,435 B2 | * | 11/2007 | Lussey et al. | 338/13 |
| 7,365,031 B2 | | 4/2008 | Swallow et al. | |
| 7,464,613 B2 | | 12/2008 | Bieck et al. | |
| 7,585,174 B2 | * | 9/2009 | Ju | 439/66 |
| 8,161,826 B1 | * | 4/2012 | Taylor | 73/862.044 |

(Continued)

FOREIGN PATENT DOCUMENTS

| | | |
|---|---|---|
| CN | 2874424 Y | 2/2007 |
| CN | 201034771 | 3/2008 |
| CN | 101231200 A | 7/2008 |
| CN | 201163226 Y | 12/2008 |
| CN | 101590315 A | 12/2009 |

(Continued)

*Primary Examiner* — Lisa Caputo
*Assistant Examiner* — Jonathan Dunlap
(74) *Attorney, Agent, or Firm* — The Hong Kong Polytechnic University

(57) ABSTRACT

A pressure sensing device includes a first conversion layer and a second conversion layer, an electrically conductive element between the first and second conversion layers, and a pair of electrically conductive yarns connected to the electrically conductive element, wherein the first and second conversion layers include at least one deformation member adapted to deform the electrically conductive element and change the resistivity of the electrically conductive element, when pressure exerts on the first and/or the second conversion layer.

16 Claims, 6 Drawing Sheets

U.S. PATENT DOCUMENTS

| | | | |
|---|---|---|---|
| 2002/0194934 A1* | 12/2002 | Taylor | 73/862.046 |
| 2004/0055396 A1* | 3/2004 | Morimoto | 73/862.045 |
| 2004/0112149 A1* | 6/2004 | Gebert | 73/862.626 |
| 2006/0162471 A1 | 7/2006 | Bieck et al. | |
| 2009/0272197 A1 | 11/2009 | Ridao Granado et al. | |
| 2012/0234105 A1* | 9/2012 | Taylor | 73/862.046 |

FOREIGN PATENT DOCUMENTS

| | | |
|---|---|---|
| EP | 1605240 A1 | 12/2005 |
| GB | 2445760 | 7/2008 |
| WO | WO95/11468 A1 * | 4/1995 |
| WO | 2005/121729 | 12/2005 |

* cited by examiner

SOFT PRESSURE SENSING DEVICE

BACKGROUND OF THE INVENTION

1. Field of the Invention

The present invention relates to pressure sensors. More particularly, the present invention relates to soft pressure sensors that are sensitive to mechanical stress.

2. Description of the Related Art

Pressure sensors have a wide range of applications from industrial to personal usage. A variety of pressure sensing technologies such as potentiometric, inductive, capacitive, piezoelectric, piezoresistive, optical, flow, and strain gauge pressure sensing have been developed for various applications. However, due to their large size, high rigidity and inflexibility, most of these conventional pressure sensing devices are not wearable by a user, and thus, not suitable to be used for personal usage. Soft and flexible pressure sensors can be used on the surface of three-dimensional shape for mapping or measuring pressures, for example, in athletic sportswears, undergarments, or patients' casts.

Several types of pressure sensors with textile-like properties have been developed. For instance, U.S. Pat. No. 7,348,506 disclosed a linear pressure sensor which comprises both electrically conductive fibers and electrically insulating fibers. If no pressure is applied, the conductive fibers are separated by the insulating fibers. While with pressure exerted on, electricity is conducted between the conductive fibers.

U.S. Pat. No. 6,543,299 disclosed a two dimensional array consisting of a lattice of individual force or pressure sensor elements comprising intersecting pairs of elongated, flexible strands or threads. Each of the strands or threads consists of a central electrically conductive wire core having a low resistivity, covered with a piezoresistive material having a relatively higher electrical resistance. The strands or threads are arranged into two parallel planar sets, one set forming parallel spaced apart rows and the other set forming parallel spaced apart columns angled with respect to the rows. Rows and columns of piezoresistive threads are retained in physical contact with one another at cross-over intersection points forming a lattice of piezoresistive junctions comprising individual force sensing elements, either by being bonded between a pair of thin, flexible, upper and lower laminating sheets, or by being interwoven to form a fabric mesh. The electrical resistance at contacting intersections decreases in a predetermined way with applied normal force, thus enabling quantitative measurement of the force by measuring the electrical resistance of the node.

U.S. Pat. No. 7,365,031 disclosed a pressure sensitive textile including two crossed electrical conductors in a woven, knitted, non-woven or plaited fabric. The conductors being normally biased apart at the crossover point with an air gap between them whereby the application of pressure normal to the plane of the fabric causes the conductors to make contact.

U.S. Pat. No. 6,826,968 disclosed a bidimensional capacitive pressure sensor includes a plurality of capacitors formed by two mutually orthogonal sets of plates parallel or substantially parallel to each other separated, at least in correspondence of the crossing areas between electrodes belonging to one and the other set, by a layer of an elastically compressible dielectric material, having an array or matrix of column plates and row plates separated, at least at crossings, by elastically compressible dielectric. The system for biasing and reading capacitances comprises circuits for selecting a column and a row plate and sequential control logic circuitry of the column and row selection circuits for generating read values of the pressure each relative to a single pixels represented by capacitor realized in the superposition or crossover area of a selected column plate with a row plate.

In E.P. Pat. No. 1,605,240, a sandwich-structured sensor with electrodes each side of a central compressible layer is disclosed. The compressible layer has a reversible effect and is applied onto a flexible base electrode layer and is covered by an insulating layer. The sensor is completed by a pattern of flexible electrodes of selected shapes applied to the insulating layer and with each electrode with a separate connection to a processor. The electrodes can be conducting fabric, i.e. with conducting thread, or can be printed onto the support layers. A capacitive pressure sensor with similar configuration is also discussed in PCT Pat. Appl. No. WO2005/121729.

The above-mentioned sensors have numerous shortcomings such as non-adjustable pressure ranges, limited service lifetime, limited sensitivity, and complexity.

In view of the above conventional pressure sensing devices, there are still needs for a pressure sensing device that is simple, compact, durable, reliable, cost-effective, lightweight and flexible with excellent sensitivity and adjustable pressure sensing ranges.

SUMMARY OF THE INVENTION

According to an aspect of the present invention, the present invention provides a pressure sensing device includes a first conversion layer and a second conversion layer, an electrically conductive element between the first and second conversion layers, and a pair of electrically conductive yarns used as connection wires in contact with the electrically conductive element, wherein the first and second conversion layers include at least one deformation member adapted to deform the electrically conductive element and change the resistivity of the electrically conductive element, when pressure exerts on the first and/or the second conversion layer.

Further features and aspects of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Embodiments of the present invention are described below in detail with reference to the accompanied drawings.

Figure 1:
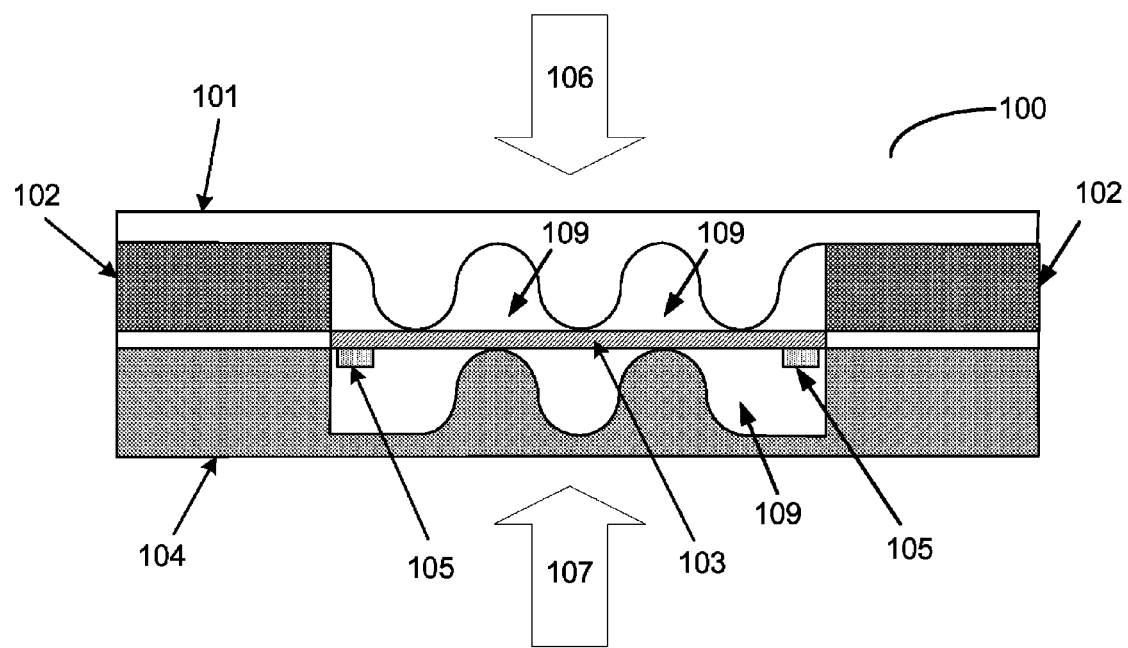
FIG. 1 illustrates a cross-sectional view of a pressure sensing device according to an embodiment of the present invention.

The present invention provides a compact pressure sensing device with excellent sensitivity. FIG. 1 illustrates an exemplary configuration of a pressure sensing device 100 includes a top conversion layer 101, a bottom conversion layer 104, and a conductive element 103 having contact with a pair of conductive yarns 105, and a pair of modulating blocks 102. The conductive element 103 is sandwiched between the top conversion layer 101 and the bottom version layer 104 with the two ends fixed to the top and bottom layers. The three components may be fixed by various methods such as adhesion or thermal bonding. In another embodiment, modulating blocks 102 with various rigidities can be inserted between the bottom conversion layer 104 and the conductive element 103, or between the top conversion layer 101 and the conductive element 103.

The top and bottom conversion layers can be made of elastic polymers (elastomers) that are capable of exhibiting elastic deformation. A pair of conductive yarns 105 can be connected to a measurement device such as a multi-meter (not shown) to measure resistivity changes of conductive element 103. Conductive element 103 can be either a conductive coating on a piece of elastic fabric, an elastic conductive film, or a kind of conductive fiber. The coating, film, or fiber, can be fabricated using a conductive mixture, which can be prepared by filling conductive fillers such as carbon black, carbon nanotubes, carbon nanofibers, intrinsically conductive polymers, metallic particles, metal fibers or metal flakes into a matrix polymer.

Each of the top and bottom conversion layers includes a grooved surface having peaks and valleys, the peaks and valleys are deformation members adapted to stretch and deform the shape of conductive element 103. The top and bottom conversion layers are aligned such that the peaks of the top conversion layer 101 match with the valleys of the bottom conversion layer 104, and the valleys of the top conversion layer 101 match with the peaks of bottom conversion layer 104, as illustrated in FIG. 1. As such, structural deformation of the conductive fabric can be increased, and hence, change of resistance ($\Delta R$) can also be increased. While smooth-grooved deformation members are illustrated in FIG. 1, various structures of the deformation members (401-406) are shown, for example, in FIG. 4.

When an external force or pressure 106 is exerted on the top conversion layer 101, the top conversion layer 101 presses against the conductive element 103, resulting in a structural deformation and elongation of conductive element 103. The structural deformation and elongation trigger an increase in resistance of conductive element 103. In addition, the grooved structures of the top and bottom conversion layers further increase the structural deformation of conductive element 103, and therefore, increase resistivity change of conductive element 103. Due to the grooved structure (deformation members), a number of air cavities 109 may be included in the pressure sensing device. Upon releasing the force or pressure, the top conversion layer moves upward because of elasticity of the two conversion layers and the conductive element. Consequently, the structure of the pressure sensing device returns to its initial state, which leads to a resistance decrease of conductive element 103.

Resistance of conductive element 103 can be measured by conducting electricity between the pair of conductive yarns 105. By measuring the change of resistivity of conductive element 103 using a multi-meter or the like, the amount of pressure exerted on the pressure sensing device 100 can be measured. Similarly, resistivity change can also be measured when pressure exerted on the bottom conversion layer (107), or from both the top (106) and bottom (107). In another embodiment, electrically conductive yarns 105 of FIG. 1 can be replaced with electrical wires.

Figure 2:
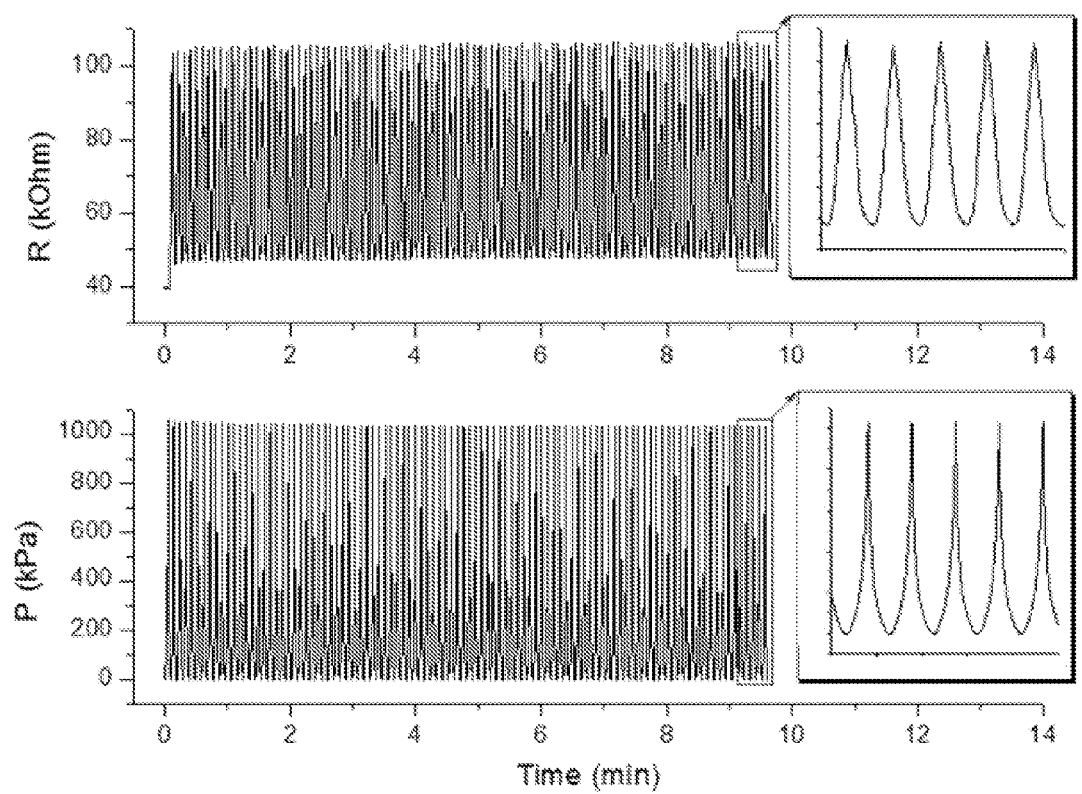
FIG. 2 illustrates the resistivity change in response to pressure change of a pressure sensing device of FIG. 1 with cyclic pressing.

FIG. 2 illustrates the resistivity change in response to pressure change of pressure sensing device 100 with cyclic pressing (pressing ratio of 40%) of the pressure sensing device 100. As shown, pressure sensing device 100 demonstrates excellent sensitivity over repeated usage. Also, the overall dimension of pressure sensing device 100 is extremely compact. In one embodiment, it can be only a few centimeters wide and a few millimeters thick. Thus, the pressure sensing device can be easily incorporated into a number of clothing items or footwears. For example, when incorporating in footwears, a pressure sensing device may be used as a weight sensor, plantar pressure distribution measuring device, or step counter, etc.

The two conversion layers transit the vertical pressing force into the extending force applied onto the conductive element. Also, due to elasticity of the conductive element 103, the pressure sensing device provides instant, reproducible, and repeatable rebounding of the conductive element to its original position, so that the resistance changes of the fabric can be repeatedly performed. A pair of modulating blocks 102 with various rigidities can be added to adjust the pressure ranges. With inclusion of the modulating blocks 102 or without use of any modulating blocks, the pressure sensitivity can be adjusted depending on its application.

For example, in a case where modulating blocks with rigidity higher than that of the top conversion layer are inserted between the top conversion layer and the conductive element, the pressure range of the sensing device will be increased. On the other hand, in a case where modulating blocks with rigidity lower than that of the top conversion layer are included in pressure sensing device, the pressure range of pressure sensing block will be decreased. For instance, with two modulation blocks of the same rigidity to the top conversion layer included, the maximum pressure range can be as high as 1 MPa with a compressing ratio of 40% (FIG. 2).

Figure 3A:
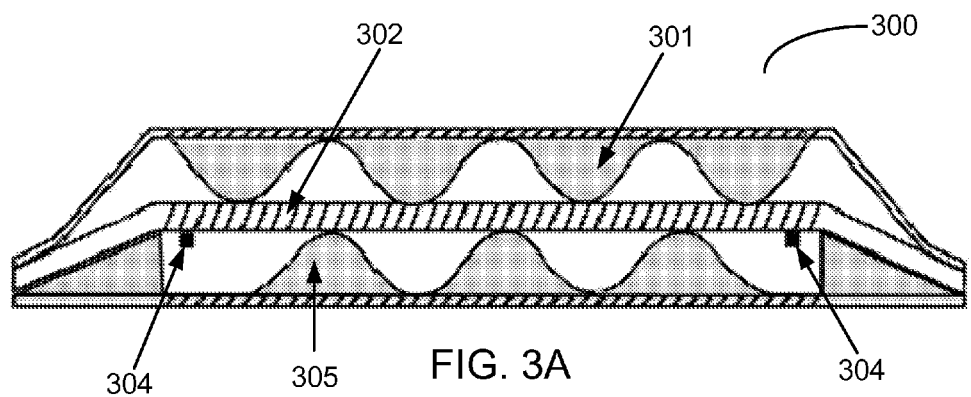
FIG. 3A illustrates a cross-sectional view of a pressure sensing device according to another embodiment of the present invention.
Figure 3B:
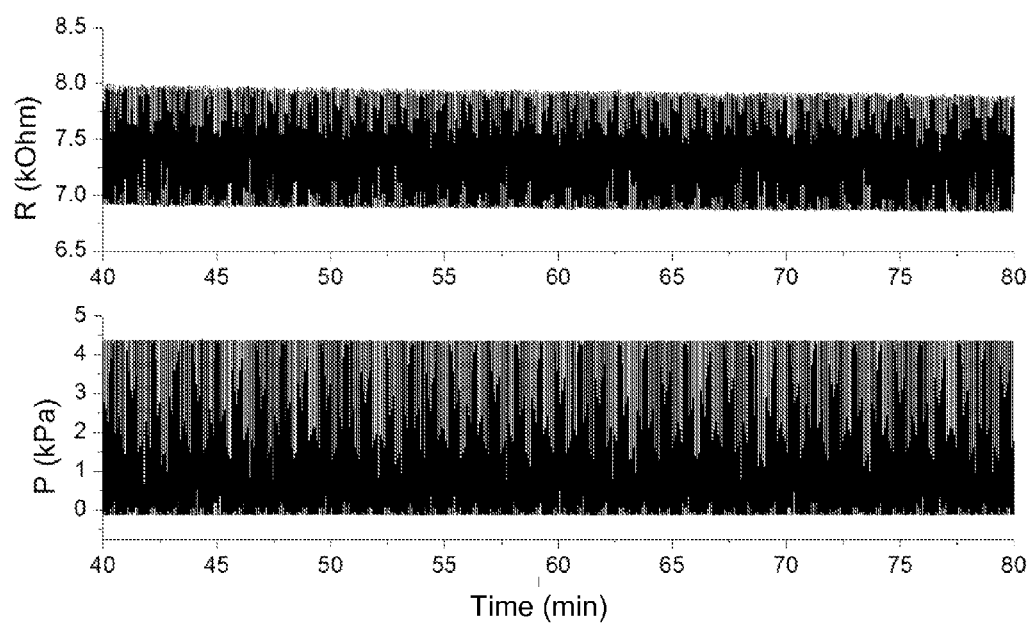
FIG. 3B illustrates the resistivity change in response to pressure change of a pressure sensing device of FIG. 3A with cyclic pressing.

FIG. 3A illustrates another exemplary embodiment of the pressure sensing device. In this embodiment, the maximum pressure can be deceased to less than 5 kPa (FIG. 3B). Pressure sensing device 300 includes a top conversion layer 301 having a plurality of deformation members, conductive element 302, bottom conversion layer 303 having a plurality of deformation members, and textile conductive yarns 304. In this embodiment, no modulation blocks are included in pressure sensing device 300. FIG. 3B illustrates the relationship of change of resistance in response to applied pressure. According to one embodiment, the thickness of the pressure sensing device is in the range of 1.0-10.0 mm, depending on the specific application of the pressure sensing device 300. The height of deformation members, the number of deformation members, and the size of the conductive element 302 are all adjustable, depending on the size and application of the sensing device 300. FIG. 3B demonstrates high repeatability of pressure sensing through continuous pressing up to 80 minutes.

Figure 4:
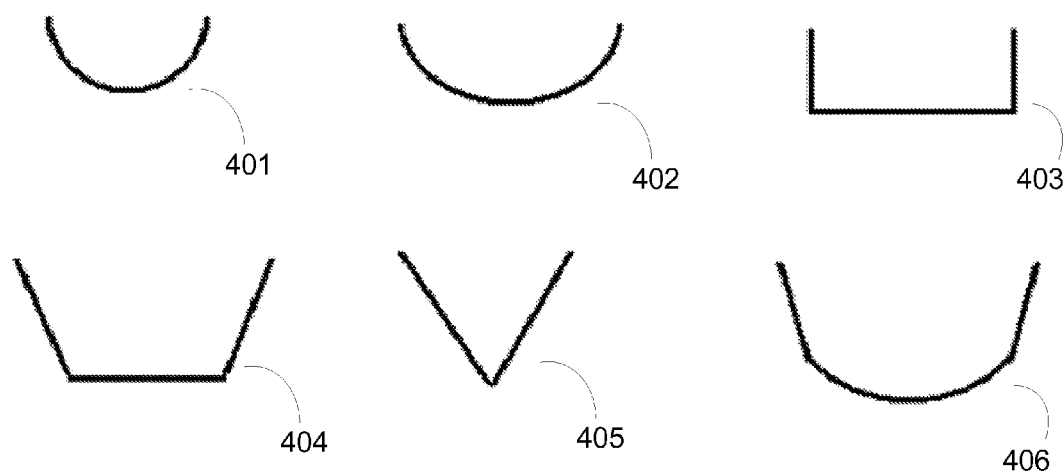
FIG. 4 illustrates various exemplary deformation members of the present invention.

The shape of the deformation members includes but not limited to the ones exemplified in FIG. 4, and the configuration of the sensing device includes but not limited to the ones exemplified in the above embodiments.

The Young's Modulus (E) of the materials for the top and bottom layers and the blocks can be ranged from 0.1 MPa to 1.0 GPa, and the ratio of Young's Modulus of the two layers and the modulating block is adjustable.

Figure 5A:
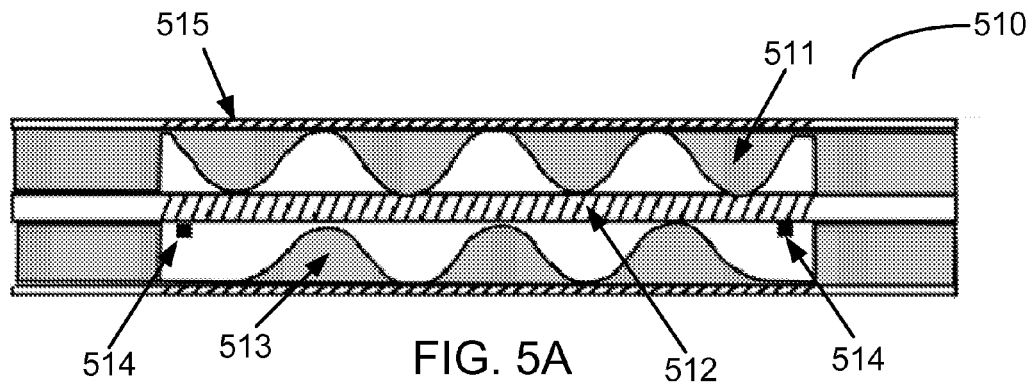
FIGS. 5A-5D illustrates various exemplary embodiments of a pressure sensing devices.

Various embodiments of the present invention are illustrated in FIGS. 5A-5D. FIG. 5A illustrates a cross-sectional view of a pressure sensing device 510 having a top conversion layer 511 with a plurality of deformation members, a conductive element 512 in contact with a pair of conductive yarns 514, and a bottom conversion layer 513 with a plurality of deformation members. Another layer 515 may be added to the top and/or bottom conversion layer for decorative or strengthening purposes.

Figure 5B:
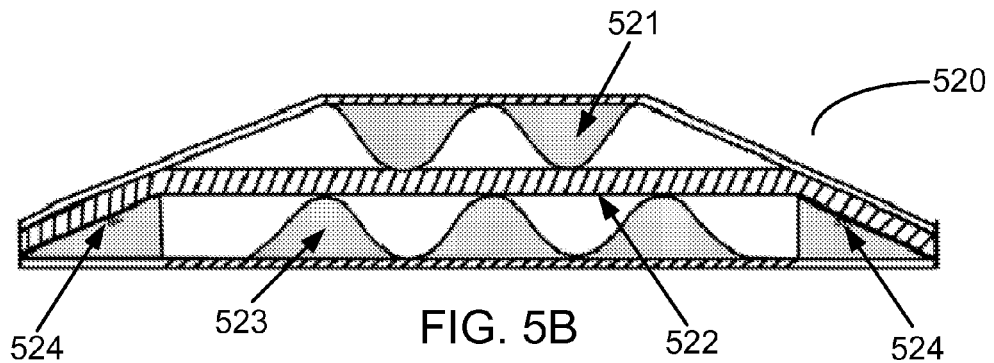

FIG. 5B illustrates a cross-sectional view of a pressure sensing device 520 with a top conversion layer 521 with a plurality of deformation members, a conductive element 522 in contact with a pair of conductive yarns 524, and a bottom layer 523 with a plurality of deformation members. The conductive yarns 524 are embedded inside the bottom conversion layer 523.

Figure 5C:
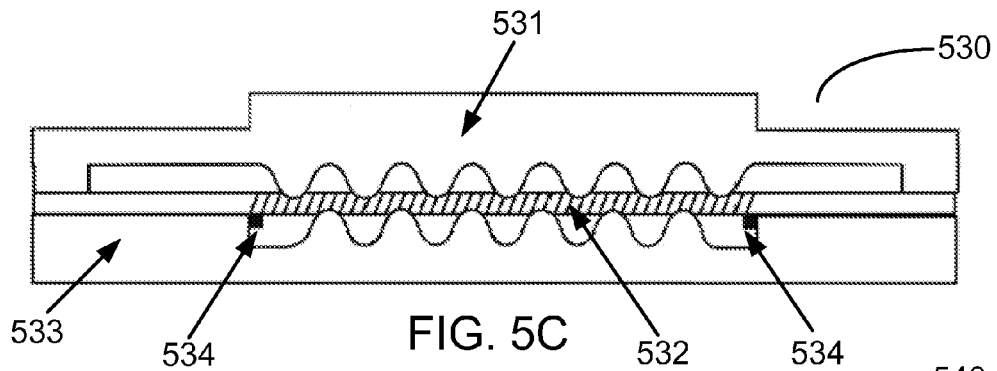

FIG. 5C illustrates a cross-sectional view of a pressure sensing device 530 with a top conversion layer 531 with a plurality of deformation members, conductive element 532 in contact with a pair of conductive yarns 534, and bottom layer 533 with a plurality of deformation members.

Figure 5D:
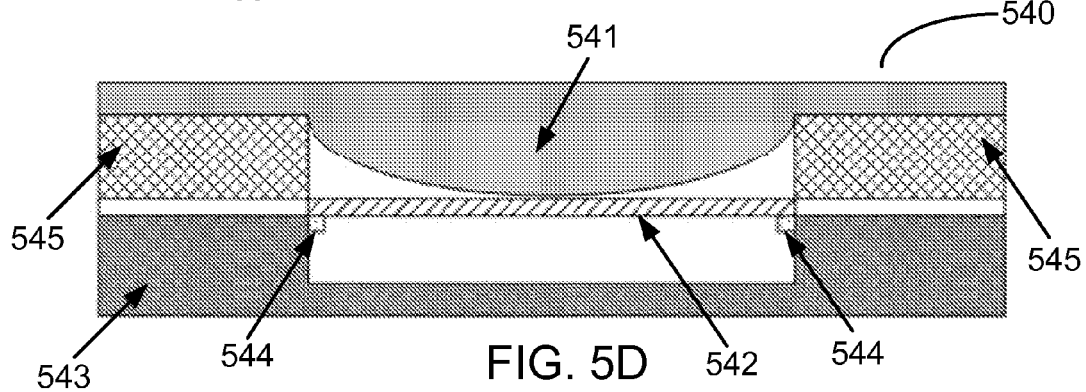

FIG. 5D illustrates a cross-sectional view of a pressure sensing device 540 with a top conversion layer 541 having a single deformation member, conductive element 542 in contact with a pair of conductive yarns 544, and bottom layer 543, and two modulating blocks 545 sandwiched between the top conversion layer 541 and the conductive element 542.

Figure 6:
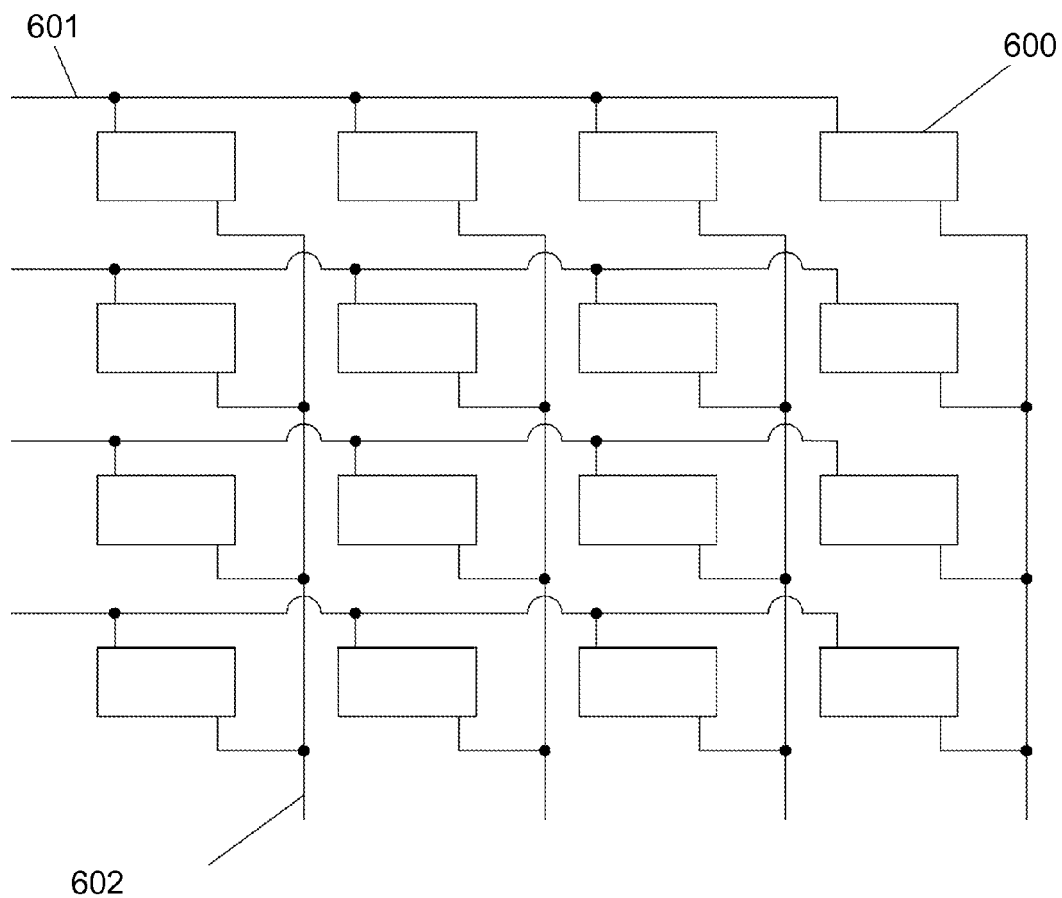
FIG. 6 illustrates an exemplary configuration of pressure sensing devices in a matrix structure.

FIG. 6 illustrates an exemplary configuration of a plurality of pressure sensing devices 600 electrically connected in a matrix structure having row lead-out wires 601 and column lead-out wires 602. These wires are connected with analog to digital converter, signal conditioning, and matrix addressing control parts. One sensor is selected with current flowing through and others are unselected without currents on at a time under the control of matrix addressing part. Voltage signal on the selected sensor from signal conditioning part is converted to digital value by analog to digital converter, then transformed to sensor resistance and pressure values. It provides a quantitative two-dimensional map of pressure sensing for various applications.

In FIG. 1, FIG. 3A, and FIGS. 5A-5D, the top and bottom conversion layers and the modulating blocks with specific (predetermined) rigidity can be fabricated with elastomers that exhibit rubbery elastic deformation. For examples, elastomers may be natural rubbers and various synthetic rubbers such as polyurethane, silicone rubbers, fluorine rubbers, copolymers of styrene-ethylene-butadiene-styrene (SEBS), styrene-butadiene-styrene (SBS), polyisobutylene, etc, or a combination thereof.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

What is claimed is:

1. A pressure sensing device comprising:
   a first conversion layer and a second conversion layer that are made with elastomer having Young's Modulus of 0.1 MPa to 1.0 GPa;
   an electrically conductive element between the first and second conversion layers; and
   a pair of electrically conductive yarns, attached to a surface of the electrically conductive element, adapted to detect resistivity change of the electrically conductive element in between the pair of electrically conductive yarns,
   wherein the first and second conversion layers include at least one deformation member adapted to deform the electrically conductive element and change the resistivity of the electrically conductive element, when pressure exerts on the first and/or the second conversion layer.

2. The pressure sensing device of claim 1, wherein the first and second conversion layers are made of elastomers with predetermined rigidity.

3. The pressure sensing device of claim 2, wherein the elastomers are natural rubbers, synthetic rubbers, polyurethanes, silicone rubbers, fluorine rubbers, copolymers of styrene-ethylene-butadiene-styrene, styrene-butadiene-styrene, polyisobutylenes, or a combination thereof.

4. The pressure sensing device of claim 1, further comprises modulating blocks that are adapted to adjust pressure ranges, the modulating blocks are inserted between the first conversion layer or the second conversion layer and the electrically conductive element.

5. The pressure sensing device of claim 4, wherein the modulating blocks having rigidity different than the first conversion layer or the second conversion layer.

6. The pressure sensing device of claim 1, wherein the pressure sensing device is adapted to incorporate into garments or footwears.

7. The pressure sensing device of claim 1, further comprises a measurement device configured to measure resistance between the pair of conductive yarns.

8. The pressure sensing device of claim 1, wherein the deformation member includes peaks and valleys, the peaks of the first conversion layer are aligned with the valleys of the second conversion layer, and the valleys of the second conversion layer are aligned with the peaks of the first conversion layer.

9. The pressure sensing device of claim 1, wherein the deformation member includes peaks and valleys on the first conversion layer or the second conversion layer.

10. The pressure sensing device of claim 1, wherein a plurality of the pressure sensing devices are electronically connected in a matrix structure.

11. The pressure sensing device of claim 1, wherein the electrically conductive element is a piece of electrically conductive fabric, a piece of electrically conductive polymer film or fiber.

12. The pressure sensing device of claim 1, wherein the pair of electrically conductive yarns are embedded in the first or second conversion layer.

13. The pressure sensing device of claim 1, wherein the pair of electrically conductive yarns are not embedded in the first or second conversion layer.

14. The pressure sensing device of claim 1, wherein the first conversion layer, the second conversion layer, and the electrically conductive element are attached by adhesives or thermal bonding.

15. The pressure sensing device of claim 1, wherein the pressure sensing device can be used as a weight sensor, a plantar pressure distribution measuring device, or a step counter.

16. A pressure sensing device comprising:
   a first conversion layer and a second conversion layer that are made with elastomer having Young's Modulus of 0.1 MPa to 1.0 GPa;
   an electrically conductive element between the first and second conversion layers; and
   a pair of electrically conductive wires, attached to a surface of the electrically conductive element, adapted to detect resistivity change of the electrically conductive element in between the pair of electrically conductive wires, wherein the first and second conversion layers include at least one deformation member adapted to deform the electrically conductive element and change the resistivity of the electrically conductive element, when pressure exerts on the first and/or the second conversion layer.

* * * * *